United States Patent [19]

Gall et al.

[11] Patent Number: 4,942,157

[45] Date of Patent: * Jul. 17, 1990

[54] 1-HYDROXY-3-(N-METHYL-N-PROPYLAMINO)PROPANE-1,1-DIPHOSPHONIC ACID, PHARMACEUTICAL COMPOSITIONS AND METHODS OF USE

[75] Inventors: Rudi Gall; Elmar Bosies, both of Mannheim, Fed. Rep. of Germany

[73] Assignee: Boehringer Mannheim GmbH, Mannheim, Fed. Rep. of Germany

[*] Notice: The portion of the term of this patent subsequent to May 22, 2007 has been disclaimed.

[21] Appl. No.: 71,320

[22] Filed: Jul. 9, 1987

[30] Foreign Application Priority Data

Jul. 11, 1986 [DE] Fed. Rep. of Germany ....... 3623397

[51] Int. Cl.$^5$ ............................................. A61K 31/66
[52] U.S. Cl. .................................. 514/108; 558/158; 562/13
[58] Field of Search ................. 260/502.5 C; 558/158; 514/108; 562/13

[56] References Cited

U.S. PATENT DOCUMENTS

| | | | |
|---|---|---|---|
| 4,054,598 | 10/1977 | Blum et al. ................... | 260/502.5 C |
| 4,134,969 | 1/1979 | Schmidt-Dunker ........ | 260/502.5 C |
| 4,327,039 | 4/1982 | Blum et al. ................... | 260/502.5 C |
| 4,621,077 | 11/1986 | Rosini et al. ................ | 514/108 |

FOREIGN PATENT DOCUMENTS

| | | |
|---|---|---|
| 2534391 | 2/1977 | Fed. Rep. of Germany. |
| 2702631 | 7/1978 | Fed. Rep. of Germany. |
| 3623397 | 1/1988 | Fed. Rep. of Germany. |
| 1002300 | 3/1983 | U.S.S.R. . |
| 1254465 | 11/1971 | United Kingdom . |

OTHER PUBLICATIONS

Von K.-H. Worms, et al., Z. Anorg. Allg. Chem., 457, 214–218 (1979).

*Primary Examiner*—Anton H. Sutto
*Attorney, Agent, or Firm*—Felfe & Lynch

[57] ABSTRACT

The present invention provides 1-Hydroxy-3-(N-methyl-N-propylamino)propane-1,1-diphosphonic acid of formula

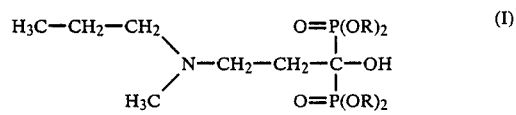

wherein R is hydrogen or $C_1$–$C_4$ alkyl and the pharmacologically acceptable salts thereof.

The present invention also provides processes for the preparation of a diphosphonic acid of formula I and pharmaceutical compositions containing it for the treatment of diseases of the calcium metabolism.

7 Claims, No Drawings

1-HYDROXY-3-(N-METHYL-N-PROPYLAMINO)-PROPANE-1,1-DIPHOSPHONIC ACID, PHARMACEUTICAL COMPOSITIONS AND METHODS OF USE

The present invention relates to 1-Hydroxy-3-(N-methyl-N-propylamino)propane-1,1-diphosphonic acid, processes for the preparation thereof and pharmaceutical compositions containing it.

Federal Republic of Germany Patent Specification No. 18 13 659 describes diphosphonic acid derivatives, of which 1-Hydroxyethane-1,1-diphosphonic acid has achieved importance as an agent for the treatment of Paget's disease. Federal Republic of Germany Patent Specification Nos. 29 43 498 and 27 02 631, European Patent Specification No. 96-931-A and Z. Anorg. Allg. Chem. 457, 214 (1979) describe 1-Hydroxy-3-(N,N-dialkylamino)propane-1,1-diphosphonic acids as good calcium complex formers which can also be used for the treatment of increased bone resorption.

Federal Republic of Germany Patent Specification No. 25 34 391 claimed 1-Hydroxy-3-(N-methyl-N-propylamino)propane-1,1-diphosphonic acid in the general formula, but it is not described as an example or as a preferred compound.

Compared with the described substances in this patent we now found that this compound which is unsymmetrically dialkylated at the nitrogen atom can also be used as a good calcium complex former, but it is much more effective for the broader treatment of calcium metabolism disturbances and of good tolerance. In particular, it can be well used where the bone formation and breakdown is disturbed, i.e. it can be used for the treatment of diseases of the skeletal system, for example osteoporosis, Paget's disease, Bechterew's diseases and the like.

However, on the basis of these properties, it can also be used for the therapy of bone metastases, urolithiasis and for the prevention of heterotopic ossifications. Due to its influence on calcium metabolism, it also forms a basis for the treatment of rheumatoid arthritis, osteoarthritis and degenerative arthrosis.

Thus, according to the present invention, there is provided 1-Hydroxy-3-(N-methyl-N-propylamino)propane-1,1-diphosphonic acid of the formula:

$$H_3C-CH_2-CH_2 \diagdown N-CH_2-CH_2-\underset{\underset{O=P(OR)_2}{|}}{\overset{\overset{O=P(OR)_2}{|}}{C}}-OH \qquad (I)$$
$$H_3C \diagup$$

wherein R is hydrogen or $C_1-C_4$ alkyl, and the pharmacologically compatible salts thereof.

The claimed di- and tetraesters are preferably the methyl, ethyl or isobutyl esters.

The compound of formula (I) according to the present invention can be preferably prepared by known processes as follows:

(a) a carboxylic acid of the formula:

$$H_3C-CH_2-CH_2 \diagdown N-CH_2-CH_2-COOH \qquad (II)$$
$$H_3C \diagup$$

is reacted with a mixture of phosphorus acid or phosphoric acid and a phosphorus halide or a phosphorus halide oxide and subsequently saponified to a free diphosphonic acid of formula (I), wherein R is hydrogen; or (b) a carboxylic acid chloride of the formula:

$$H_3C-CH_2-CH_2 \diagdown N-CH_2-CH_2-COCl \qquad (III)$$
$$H_3C \diagup$$

is reacted with a trialkyl phosphite of the general formula:

$$P(OR')_3 \qquad (IV)$$

wherein R' is an alkyl radical containing up to 4 carbon atoms, preferably a methyl, ethyl or isobutyl radical, to give an acyl phosphonate of the formula:

$$H_3C-CH_2-CH_2 \diagdown N-CH_2-CH_2-\overset{O}{\overset{\|}{C}}-\overset{O}{\overset{\|}{P}}(OR')_2, \qquad (V)$$
$$H_3C \diagup$$

wherein R' has the above-given meaning, which is subsequently reacted with a dialkyl phosphite of the general formula:

$$H-\overset{O}{\overset{\|}{P}}(OR')_2, \qquad (VI)$$

wherein R' has the above-given meaning, to give a diphosphonate of the formula:

$$H_3C-CH_2-CH_2 \diagdown N-CH_2-CH_2-\underset{\underset{O=P(OR')_2}{|}}{\overset{\overset{O=P(OR')_2}{|}}{C}}-OH, \qquad (VII)$$
$$H_3C \diagup$$

wherein R' has the above-given meaning, and the resultant tetraester is optionally saponified to the corresponding diester or free 1-Hydroxy-3-(N-methyl-N-propylamino)propane-1,1-diphosphonic acid of formula (I); or (c) a compound of the general formula:

$$H_3C-CH_2-CH_2-NH-CH_2-CH_2-\underset{\underset{O=P(OR')_2}{|}}{\overset{\overset{O=P(OR')_2}{|}}{C}}-OH, \qquad (VIII)$$

wherein R' has the above-given meaning, is methylated and the resultant tetraester is optionally saponified to the corresponding diester or free 1-Hydroxy-3-(N-methyl-N-propylamino)propane-1,1-diphosphonic acid of formula (I) and, if desired, the compound thus prepared is converted into its pharmacologically compatible salts.

The carboxylic acid of formula (II) used in process (a) is reacted with 1 to 5 and preferably 2 to 3 mol phosphorus trihalide or phosphorus trihalide oxide at a temperature of 80° to 130° C. and preferably of 80° to 100° C. The reaction can also be carried out in the presence of diluents, for example halogenated hydrocarbons, especially chlorobenzene or tetrachloroethane, or also dioxan. The subsequent hydrolysis takes place by boiling with water but preferably with semiconcentrated hydrochloric or hydrobromic acid.

As phosphorus trihalides in the above-mentioned processes, there can be used, for example, phosphorus trichloride or phosphorus trimbromide, as phosphorus trihalide oxide can be taken phosphorus trichloride oxide.

In the case of process (b), the acid chloride of formula (III) is reacted with the trialkyl phosphite of formula (IV) at a temperature of 0° to 60° C. and preferably of 20° to 40° C. The reaction can be carried out without a solvent or also in the presence of inert solvents, for example diethyl ether, tetrahydrofuran, dioxan or also halogenated hydrocarbons, for example methylene chloride. The acyl phosphonate of general formula (V) formed as intermediate can be isolated or further reacted directly. The subsequent reaction is carried out in the presence of a weak base, preferably of a secondary amine, for example dibutylamine, at a temperature of 0° to 60° C. and preferably of 10° to 30° C.

In the case of the reductive alkylation according to process (c), a mixture of secondary amine of general formula (VIII) and formaldehyde or of the acetal thereof is treated in the presence of a hydrogenation catalyst, for example palladium on charcoal or nickel, with hydrogen at atmospheric or increased pressure or with the use of formic acid as reducing agent. In addition, methylation of the secondary amine of general formula (VIII) can be carried out especially advantageously according to the phase transfer process with dimethylsulphate.

The tetraalkyl esters possibly obtained in the processes (b) and (c) can be saponified to the corresponding diesters or to the free 1-Hydroxy-3(N-methyl-N-propylamino)propane-1,1-diphosphonic acid. The saponification to diesters usually takes place by treating the tetraalkyl esters with an alkali metal halide, preferably sodium iodide, in an appropriate solvent, for example acetone, at ambient temperature. There is hereby obtained the symmetrical diester/disodium salt which, if desired, can be converted into the diester/diacid by means of an acidic ion exchanger. The saponification to the free diphosphonic acids usually takes place by boiling with hydrochloric or hydrobromic acid. However, a cleavage with a trimethylsilyl halide, preferably the bromide or iodide, can also be carried out. On the other hand, the free diphosphonic acid can be converted again into the tetraalkyl esters by boiling with orthoformic acid alkyl esters. The free 1-Hydroxy-3-(N-methyl-N-propylamino)propane-1,1-diphosphonic acid of formula (I) can be isolated as the free acid or in the form of its mono- or dialkali metal salt. The alkali metal salt can usually be readily purified by reprecipitation from water/methanol or from water/acetone.

As pharmacologically acceptable salts, there are preferably used the alkali metal or ammonium salts which can be prepared in the usual way, for example by titration of the compounds with inorganic or organic bases, for example sodium or potassium hydrogen carbonates, aqueous solutions of sodium or potassium hydroxide or aqueous solutions of ammonia or of amines, for example trimethyl or triethylamine.

The compound of formula (I) according to the present invention and the salts thereof can be administered enterally or parenterally in liquid or solid form. For this purpose, there can be used all conventional forms of administration, for example tablets, capsules, dragees, syrups, solutions, suspensions and the like. As injection medium, it is preferred to use water which contains the additives usual in the case of injection solutions, for example stabilising agents, solubilising agents and buffers. Additives of this kind include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Liquid carrier materials for injection solutions must be sterile and are preferably placed in ampoules. Solid carrier materials include, for example, starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats and solid high molecular weight polymers (such as polyethylene glycol). Compositions suitable for oral administration can, if desired, also contain flavouring and sweetening agents.

The dosage can depend upon various factors, such as the mode of administration, species, age and/or individual condition. The dosages to be administered daily are about 1 to 1000 mg in the case of humans preferably 10 to 200 mg and can be given once or several times per day.

The following examples illustrate some of the process variants which can be used for the synthesis of the compound according to the present invention. The structure of this compound was verified by $^1H-$ and $^{31}P$-NMR spectroscopy and the purity by means of $^{31}P$-NMR spectroscopy, thin layer electrophoresis (cellulose, oxalate buffer of pH 4.0) and by means of C, H, N, P and Na analyses. For the characterisation of the compound, there is given the $M_{rel}$ value (relative mobility) referred to pyrophosphate ($M_{rel}=1.0$).

EXAMPLE 1

1-Hydroxy-3-(N-methyl-N-propylamino)propane-1,1-diphosphonic aicd 18 g 3-(N-methyl-N-propylamino)prooionic acid are kept for 12 hours at 100° C. with 15 g. phosphorus acid and 32 ml. phosphorus trichloride in 90 ml. chlorobenzene. The solvent is then decanted off and the residue is stirred under reflux with 250 ml. 6N hydrochloric acid for 2 hours. Insoluble material is filtered off and the filtrate is concentrated and applied to a column of Amberlite IR 120 (H+ form). The elution with water is monitored electrophoretically. The desired fractions are combined, evaporated and stirred up with acetone/methanol and the crystals obtained are isolated. There are thus obtained 14.1 g. of crude product. After recrystallisation from water/methanol, there are obtained 9.8 (27% of theory) of analytically pure product in the form of the sesquihydrate; $M_{rel}=0.4$; m.p. 96°-102° C., 108° C. (decomp.).

The starting material is obtained as follows:

N-methyl-N-propylamine (J.A.C.S., 79 4720/1957) is reacted with methyl acrylate in toluene in the molar ratio 1:3 and the ester obtained in a yield of 84% of theory is, without distillation, saponified with 1N aqueous sodium hydroxide solution. The oily acid is thus obtained in a yield of 92% of theory and is used without further purification.

EXAMPLE 2

10 g 3-(N-methyl-N-propylamino)propionic acid are heated to 80° C. with 11.4 g. phosphorus acid. The melt is mixed with 12 ml. phosphorus trichloride and kept at the same temperature for 16 hours.

Excess phosphorus trichloride is distilled off, 140 ml. 6N hydrochloric acid are added thereto and the reaction mixture is stirred for 3 hours at 100° C. It is then filtered, the filtrate is concentrated in vacuum and the oil obtained is purified by ion exchanger chromatography in the manner described in Example 1. Yield 6.95 g. (35% of theory) as sesquihydrate; $M_{rel}=0.4$;
m.p. 96°–102° C., 108° C. (decomp.).

EXAMPLE 3

In a manner analogous to that described in Example 2, 15 g. 3-(N-methyl-N-propylamino)propionic acid are heated to 80° C. with 17 g. phosphorus acid and 19 ml. phosphorus trichloride oxide. After 18 hours at 80° C. the excess phosphorus trichloride oxide is distilled off and the residue is saponified by heating it with 210 ml 6N hydrochloric acid for 2 hours. The crude product was purified by ion exchanger chromatography in the manner described in Example 1 (Amberlite-IR 120, H+ form). $M_{rel}=0.4$, Yield 16.2 g (54% of theory) as sesquihydrate after recrystallisation from water/methanol;
m.p. 96°–102° C., 108° C. (decomp.).

Methods

Male Wistar rats weighing about 160 g. were thyroparathyroidectomized on day 1. On day 5, the success of the operation was controlled by measuring calcemia after a night fasting. From that day on, all the animals were group-fed, that means all of them ate the same quantity of food. Furthermore, the animals received then daily for 3 days 2 subcutaneous injections, one containing 25/μg of ethyl p-[(E)-2-(5,6,7,8-tetrahydro-5,5,8,8-tetramethyl-2-naphthyl)-1-propenyl]benzoat, a synthetic retinoid the other one the bisphosphonate to be tested. Additionally, all animals were given 2/μg of thyroxine the first and last day of treatment. 24 h after the last injection of the retinoid and the bisphosphonate and after one night fasting, blood was taken by retroorbital puncture under ether anesthesia. Plasma calcium was then analyzed by means of atomic absorption.

The bisphonsphonates were given first at a dose of 0.1 mg P/kg in a volume of 2 ml/kg. In a second time, the active compounds were injected at 0.01 and 0.001 mg P/kg.

During all these experiments, the animals received water ad libitum. The diet given was Kliba 331, which contains 1.0 g. Ca/100 g., 0.8 g. Pi/100 g., and to which 800 I. U. of vitamin D3/kg. was added. Each group consisted of two or more animals.

| | mg P/kg s. c. | | |
|---|---|---|---|
| | 0.001 | 0.01 | 0.1 |
| A | 0 | + | ++++ |
| B | | + | +++ |
| C | + | +++ | ++++ | o = degradation of hypercalcemia from −0.99 to +0.99 mg %
(+) = degradation of hypercalcemia from 1.0 to 1.99 mg %
+ = degradation of hypercalcemia from 2.0 to 2.99 mg %
++ = degradation of hypercalcemia from 3.0 to 3.99 mg %
+++ = degradation of hypercalcemia from 4.0 to 4.99 mg %
++++ = degradation of hypercalcemia from >5.0
A = 1-Hydroxy-3(N,N-dimethylamino)propane-1,1-diphosphonic acid
B = 3-(N,N-diethylamino)-1-hydroxypropane-1,1-diphosphonic acid
C = 1-Hydroxy-3-(N-methyl-N-propylamino)propane-1,1-diphosphonic acid
A and B are compounds of DE-PS 25 34 391

What is claimed is:

1. A diphosphonate compound of the formula

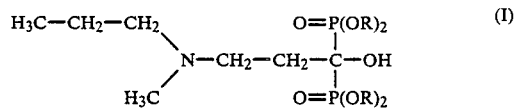

wherein R is hydrogen, and the pharmacologically acceptable salts thereof.

2. A pharmaceutical composition for the treatment or prophylaxis of calcium metabolism disturbance or disease containing an effective amount of at least one compound of claim 1 in pharmaceutically acceptable carrier.

3. A pharmaceutical composition for the treatment or prophylaxis of calcium metabolism disturbance or disease containing an effective amount in a pharmaceutically acceptable carrier of 1-hydroxy-3-(N-methyl-N-propylamino)propane-1,1-diphosphonic acid.

4. A method for the treatment or prophylaxis of calcium metabolism disturbance or disease comprising administering a pharmaceutically effective amount of the compound of claim 1.

5. A method for the treatment or prophylaxis of calcium metabolism disturbance or disease comprising administering a pharmaceutically effective amount of 1-hydroxy-3-(N-methyl-N-propylamino)propane-1,1-diphosphonic acid.

6. The method of claim 4 wherein 0.001–10 mg P/Kg of the pharmaceutically acceptable diphosphonate compound are administered per day.

7. The method of claim 5 wherein 0.01–10 mg P/Kg of the pharmaceutically acceptable disphosphonate are administered per day.

* * * * *

UNITED STATES PATENT AND TRADEMARK OFFICE
CERTIFICATE OF CORRECTION

PATENT NO. : 4,942,157
DATED      : July 17, 1990
INVENTOR(S): Rudi Gall, et al.

It is certified that error appears in the above-identified patent and that said Letters Patent is hereby corrected as shown below:

Col. 2, line 64:  after "1 to 5" insert -- and preferably 2 to 3 mol phosphorous acid or phosphoric acid and 1 to 5 --.

Col. 4, line 32:  change "$^1$H- and $^{31}$P-NMR" to -- $1_H$- and 31p-NMR --.

Col. 4, line 33:  change "$^{31}$P-NMR" to -- 31p-NMR --.

Col. 4, line 42:  change "aicd" to -- acid --.

Col. 4, line 44:  change "prooionic" to -- propionic --.

Signed and Sealed this

Eleventh Day of August, 1992

*Attest:*

DOUGLAS B. COMER

*Attesting Officer*   *Acting Commissioner of Patents and Trademarks*